United States Patent [19]
Tepper et al.

[11] Patent Number: 6,024,691
[45] Date of Patent: Feb. 15, 2000

[54] CERVICAL COLLAR WITH INTEGRATED ELECTRICAL CIRCUITRY FOR ELECTROMAGNETIC FIELD THERAPY

[76] Inventors: John C. Tepper, 1400 Harmony Dr., Carrollton, Tex. 75006; Peter Kuo, 6041 Village Bend Dr., Dallas, Tex. 75206; Michael C. Dinsdale, 1003 N. Park, Richardson, Tex. 75081

[21] Appl. No.: 09/084,525

[22] Filed: May 26, 1998

[51] Int. Cl.$^7$ .................................................. A61N 1/00
[52] U.S. Cl. .................................. 600/13; 600/14; 600/9; 600/15
[58] Field of Search ................................ 600/13, 15, 2, 600/14, 9–12; 128/876; 606/33

[56] References Cited

U.S. PATENT DOCUMENTS

| | | | |
|---|---|---|---|
| 4,456,001 | 6/1984 | Pescatore | 128/1.5 |
| 4,501,265 | 2/1985 | Pescatore | 128/1.5 |
| 4,548,208 | 10/1985 | Niemi | 128/419 |
| 4,561,426 | 12/1985 | Stewart | 128/1.5 |
| 4,616,629 | 10/1986 | Moore | 128/1.5 |
| 4,635,643 | 1/1987 | Brown | 128/653 |
| 4,662,378 | 5/1987 | Thomis | 128/644 |
| 4,932,951 | 6/1990 | Liboff et al. | 606/13 |
| 4,974,114 | 11/1990 | Kammerer | 361/159 |
| 5,088,976 | 2/1992 | Liboff et al. | 600/13 |
| 5,478,303 | 12/1995 | Foley-Nolan et al. | 600/15 |
| 5,743,844 | 4/1998 | Tepper et al. | 600/14 |

*Primary Examiner*—Max Hindenburg
*Assistant Examiner*—Brian Szmal
*Attorney, Agent, or Firm*—Baker & Botts, L.L.P.

[57] ABSTRACT

A collar (100) for providing PEMF therapy for the cervical region of the spine. The collar (100) has a single transducer coil (104) and requires no secondary coil. The electronics for driving the coil are contained in a housing (101) that is integral to the collar 100. The housing (101) may also contain a battery for powering the coil (104), whose power usage is sufficiently reduced so as to require only a small battery.

21 Claims, 5 Drawing Sheets

| PARAMETER | SYMBOL | REQUIREMENT | UNITS |
|---|---|---|---|
| BURST INTERVAL | Tbi | 670 ± 3 | ms |
| FIRST PULSE WIDTH (+) | tpwf (+) | 33 ± 3 | µs |
| PULSE WIDTH (+) | tpw (+) | 65 ± 3 | µs |
| PULSE WIDTH (−) | tpw (−) | 195 ± 10 | µs |
| PULSES PER BURST | $N_p$ | 99 | − |

CERVICAL COLLAR WITH INTEGRATED ELECTRICAL CIRCUITRY FOR ELECTROMAGNETIC FIELD THERAPY

TECHNICAL FIELD OF THE INVENTION

This invention relates generally to electromagnetic field therapy that promotes healing of bones and other body tissues, and more particularly to a collar for cervical electromagnetic field therapy.

BACKGROUND OF THE INVENTION

Pulsed electromagnetic fields (PEMF) are low-energy, time-varying magnetic fields that are useful for treating therapeutically resistant problems of the musculoskeletal system. Those problems include spinal fusion, un-united fractures (or non-union fractures), failed arthrodeses, osteonecrosis, and chronic refractory tendinitis, decubitus ulcers and ligament, tendon injuries, osteoporosis, and Charcot foot. For PEMF therapy, an electromagnetic transducer coil is placed in the vicinity of the musculoskeletal injury such that pulsing the PEMF transducer produces an applied field that penetrates to the underlying bone.

For cervical PEMF therapy, an electromagnetic transducer coil is placed at the back of the patient's neck, such that the applied field from the coil penetrates to the cervical spine. One conventional approach is to use a flat oval-shaped transducer coil that is attached to a conventional cervical collar. This approach is disadvantageous because the transducer coil does not cover the entire back of the neck and the applied field does not penetrate below the vertebra at the bottom of the neck. A different approach uses a triangular-shaped transducer connected to the back of the patient's neck with a collar device.

These conventional PEMF cervical collars have an electronics circuit whose housing is separate from the rest of the collar. This housing must be attached around the patient's waist or placed atop a table next to the patient. A battery may be contained within the same housing, but the result is that the housing is heavy and cumbersome.

Until recently, prior art PEMF cervical collars have used both a primary coil and a secondary coil for providing the PEMF signal. However, a recently developed coil and drive circuit design permits the use of only a single coil, which results in a more compact and energy efficient coil. This design is described in U.S. Pat. No. 5,743,844, entitled "High Efficiency Pulsed Electromagnetic Field (PEMF) Stimulation Therapy Method and System", to Tepper et al., assigned to AMEI Technologies Inc.

SUMMARY OF THE INVENTION

One aspect of the invention is a collar for providing electromagnetic field therapy to a cervical region. A semi-rigid neck band has an approximately semicircular top profile with two open ends, for placement around the back of a human neck. Two chest straps are each connected to an open end of the neck band. An electrical circuitry housing is attached between the second ends of the chest straps. This housing contains electrical circuitry for generating an electrical PEMF drive current. A transducer coil attached to the neck band generates an electromagnetic field in response to the drive signal. Typically, the electromagnetic field is a pulsed field according to a predetermined sequence of pulses, which may be the result of a PEMF program generated by processor circuitry that is also stored in the housing.

The single-coil design is driven by bi-phasic drive current, and can be powered by a small battery. This permits the entire electrical circuitry, including a battery, to be contained within a small lightweight housing that is integral to the collar itself. There is no need to run leads to a separate electronics unit that must be worn around the waist or placed atop a table.

The coil can be easily shaped to conform to the back of the neck, thereby delivering the electromagnetic field to the entire cervical region of the patient. No strap is required to encircle the patient's neck, which adds to patient comfort. The collar can be adjusted to accommodate various patient sizes.

DETAILED DESCRIPTION

Collar for PEMF Therapy

Figure 1A:
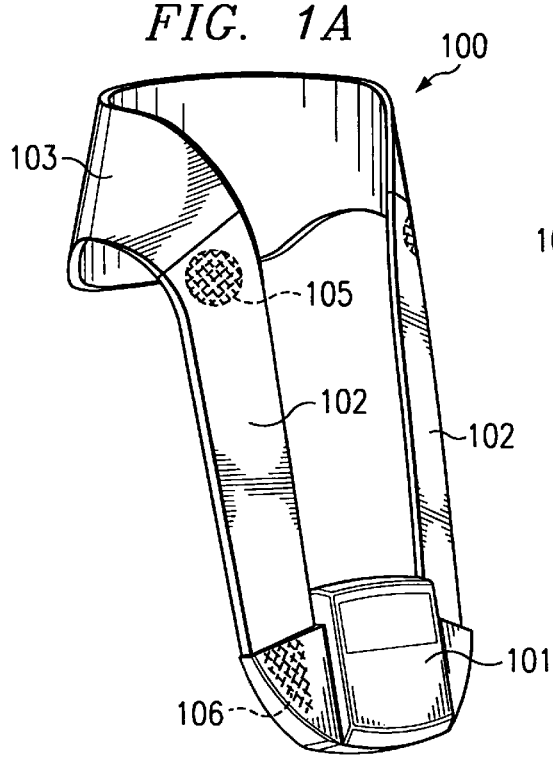
FIGS. 1A through 1D are component diagrams of a cervical PEMF therapy collar according to the invention.

FIGS. 1A through 1D are various views of a collar 100 for electromagnetic field therapy in accordance with the invention. In operation, the collar 100 is worn by the patient and emits an electromagnetic field at the cervical region of the spine. As explained below, the electromagnetic field is typically a pulsed field for PEMF (pulsed electromagnetic field) therapy, but the invention may be used to provide any desired output signal.

Collar 100 may be comfortably worn by the patient, either under or on top of other clothing. Collar 100 provides soft but semi-rigid support of the cervical region. Collar 100 can be worn outside a neck brace or can be worn alone without a brace.

Collar 100 has an electronics housing 101, attached between the lower ends of a pair of chest straps 102. Thus, housing 101 is integral to collar 100 in the sense that it need not be separately worn, carried, or placed near the patent during use.

The upper ends of chest straps 102 are attached to a neck band 103. Neck band 103 fits upon the back of the patient's neck while straps 102 are placed over the patient's shoulders. Electronics housing 101 rests on the chest or stomach of the patient, as dictated by the length of straps 102 and the patient's size.

Neck band 103 is substantially semicircular in shape. Its height is appropriate for the length of a human neck. A flanged portion at the bottom of neck band 103 drops below the patient's neck where neck band 103 covers the spine.

A transducer coil 104 is attached to the inner surface of neck band 103. In other embodiments, coil 104 may be attached to the outer surface of neck band 103 or embedded within neck band 103. Coil 104 forms a closed oval-shaped loop. As an alternative to being flat, coil 104 may be contoured with a semi-circular shape, such that the plane of the coil 104 is curved and permits coil 104 to conform to the back of the neck as well as to wrap around each side of the neck. Like neck band 103, coil 104 has a flanged portion that drops below the neck to cover a portion of the spine.

As explained below in connection with FIGS. 4–8, transducer coil 104 provides the electromagnetic field. Coil 104 is especially designed to be compact and lightweight, and to have reduced power usage.

Figure 1B:
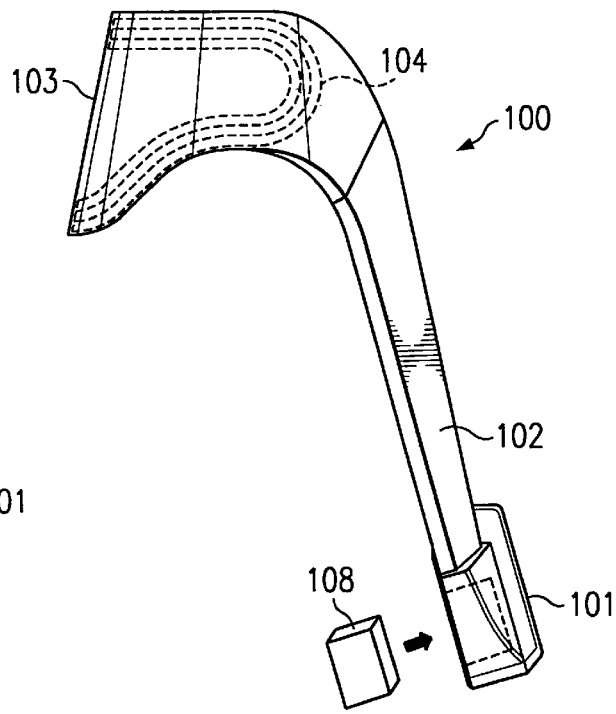

As illustrated in FIG. 1B, collar 100 is battery operated. More specifically, the power for driving coil 104 is DC power from a battery 121 inserted into a battery compartment 122 in housing 101. Because of the reduced power requirements of coil 104, only a small battery is required, such as a conventional 9 volt battery. Thus, housing 101 may contain the battery as well as all electrical circuitry other than coil 104. In other embodiments, collar 100 might (alternatively or additionally) have an AC adapter and appropriate regulator circuitry.

Straps 102 and neck band 103 are comprised of a semi-rigid material. Ideally, the material is sufficiently rigid so that straps 102 and neck band 103 generally retain their pre-formed shapes. Neck band 103 is necessarily a housing for coil 104, and in the example of FIGS. 1A–1D, its shape is generally the same as that of coil 104. However, neck band 102 may have any shape appropriate for placement around the back of the neck.

At the same time, the semi-rigid neck band 103 and straps 102 are sufficiently flexible to permit the patient or a health care professional to adjust the anatomical contour. Examples of suitable materials are KYDEX material and polyurethane.

In some embodiments, neck band 103 may be elastically deformable, but when coil 104 is bent to a desired shape, neck band 103 will retain the shape of coil 104. In other embodiments, it may be neck band 103 that holds the set. Thus, it is not necessary that both neck band 103 and coil 104 have the same rigidity or be deformable in the same manner. However, either neck band 103 or coil 104 (or a third element not shown attached to neck band 103) may be a "structural" element in the sense that it holds a desired shape around the patient's neck in response to applied pressure for adjustment purposes. Once this shape is attained, the other element(s) are sufficiently flexible so as to conform to this shape. These other element(s) may or may not have a "memory" such that in the absence of the structural element, they would go back to their original shape after pressure is released.

In the embodiment of FIGS. 1A–1D, straps 102 join neck band 103 by means of a pivot mechanism 105. Pivot mechanism 105 permits straps 102 to be adjusted outward or inward depending on the size and preference of the patient. This adjustability permits neck band 103 to better rest against the patient's neck.

One implementation of pivot mechanism 105 might be mating Velcro patches attached to the respective mating ends of straps 102 and neck band 103. These Velcro patches 105 permit neck band 103 attached to collar 100 at varying angles. Alternatively, pivot mechanism 105 could comprise a rotatable connection between chest straps 102 and neck band 103.

At least one strap 102 is detachable at its lower end from control housing 101 by means of an attachment mechanism 106. This permits collar 100 to be easily placed on a patient by disconnecting the strap 102, placing the collar 100 patient, and then reattaching strap 102. One example of an implementation of attachment mechanism 106 is mating patches of Velcro attached to the lower end of strap 102 and to control housing 101.

Although not shown in FIGS. 1A–1D, the design of the collar 100 permits straps 102 and neck band to be encased with a fabric pouch. This pouch enhances the appearance and comfort of collar 100 and also protects collar 100 from wear and tear.

Figure 1C:
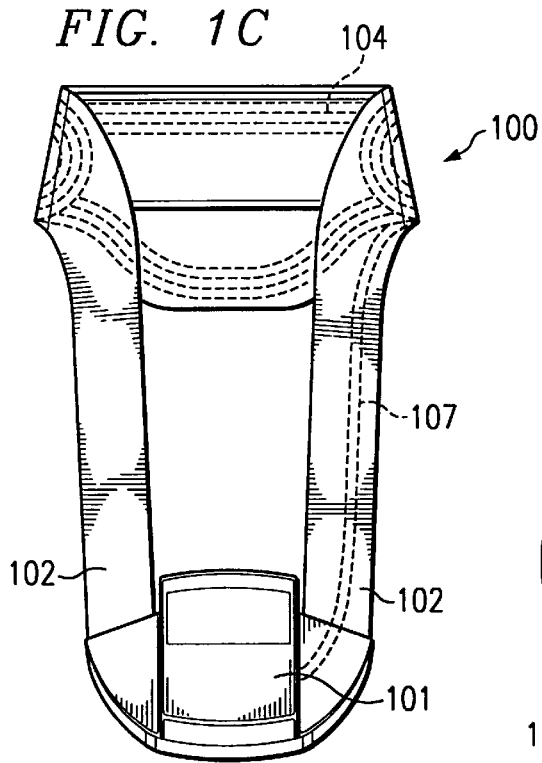

The front view of FIG. 1C further illustrates an electrical lead 107, which connects the electronics circuitry contained in electronics housing 101 to transducer coil 104. Various means for connecting the lead 107 to the ends of coil 104 may be used. For example, a very small circuit board (not shown) could be embedded in neck band 103 or in chest straps 102 and provide a surface for soldering the connections.

Figure 1D:
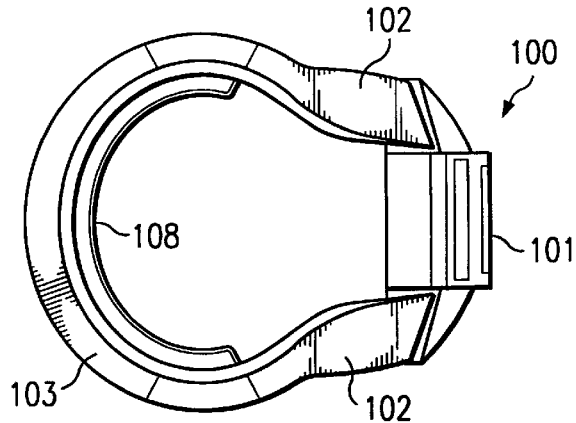

The top view of FIG. 1D illustrates the approximately semicircular top profile of collar neck band 103. A soft neck band insert 108 is operable to attach and disconnect from the inside of neck band 103. Insert 108 permits neck band 103 to accommodate different neck sizes.

Figure 2:
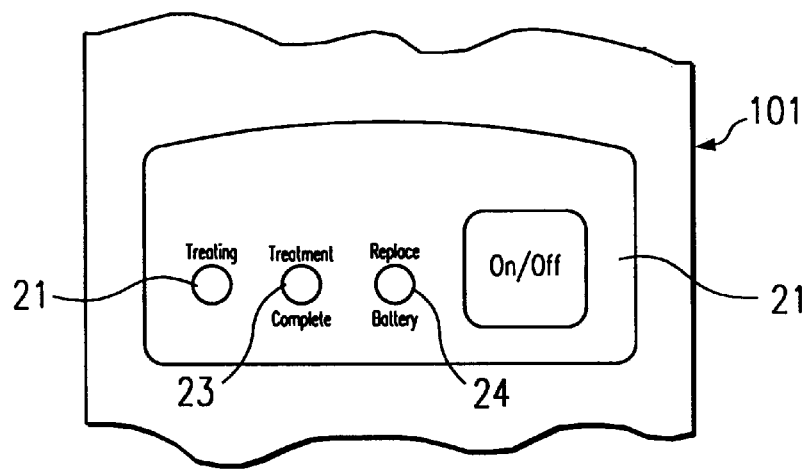
FIG. 2 illustrates a control panel for the electrical housing of FIG. 1.

FIG. 2 illustrates an example of control panel 101a for housing 101. An on/off switch 21 as well as various indicator lights 22–24 are provided. These indicator lights include a light 22 indicating that treatment is in process, a light 23 indicated that treatment is complete, and a light 24 indicating a low battery condition. In other embodiments, control panel 101a could be easily located elsewhere on collar 100 or provided as a control box from housing 101.

PEMF Transducer Design and Fabrication

Figure 3:
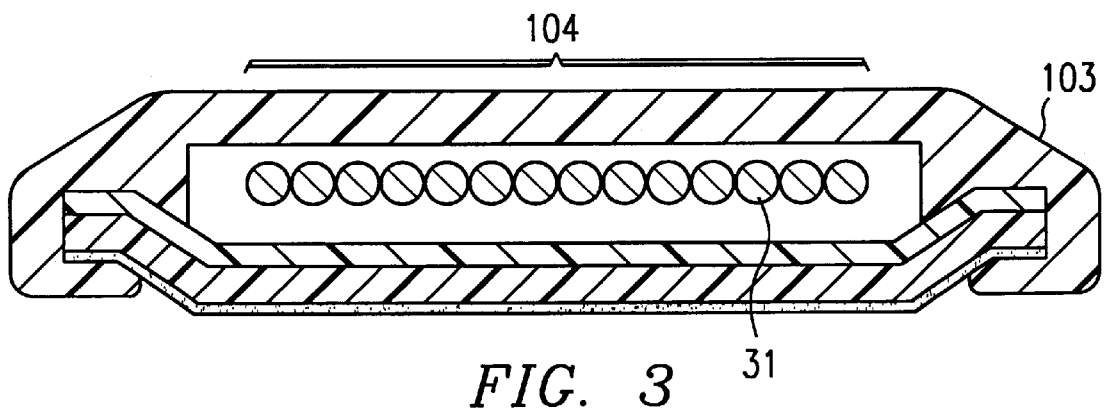
FIG. 3 is an exemplary winding pattern for the transducer coil of FIG. 1.

FIG. 3 is a cross-sectional view of transducer coil 104 according to one embodiment of the present invention. As shown, coil 104 may have a substantially flat cross-sectional profile, which is a result of a flat-wound construction.

In FIG. 3, transducer coil 104 comprises a single set of primary windings 31. Windings 31 are encapsulated in a semi-rigid shell, which comprises neck band 103. In other embodiments, coil 104 may have two or more primary windings in parallel, one layered on top of the other. However, a feature of the invention is that there is only a single (primary) coil 104, in the sense that coil 104 has only two terminal connection points and there is no secondary coil.

For an exemplary embodiment, windings 31 are comprised of 18 gauge wire. The winding material can be a commercially available hook-up wire.

As stated above, neck band 103 may be a polyurethane-type elastomer material, available commercially. Other materials for neck band 103 can be used to provide different degrees of rigidity. As illustrated in FIG. 3, additional layers of material 32 and 33 may be used. Layers 31–33 may wrap around the coil 31 or be substantially flat under coil 31.

Control and Drive Electronics

Figure 4:
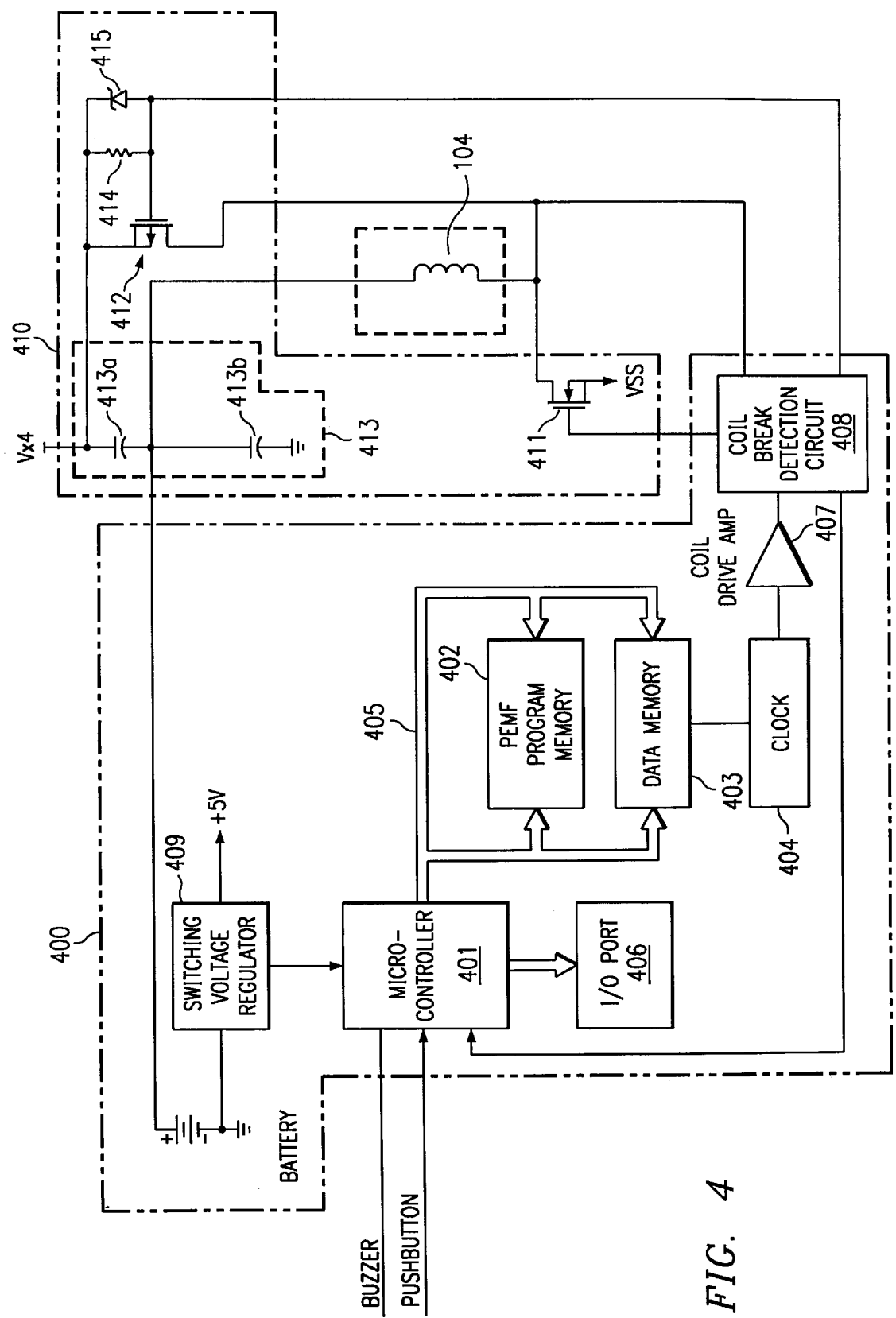
FIG. 4 is a schematic block diagram of the electronic circuitry contained within the housing and of the transducer coil.

FIG. 4 is a partly schematic and partly block diagram of the electrical circuitry of the invention. In the example of FIG. 4, this circuitry provides a pulsing bi-phasic current to transducer coil 104 at predetermined intervals, thereby activating the PEMF output signal according to a prescribed pre-programmed PEMF regimen.

Except for coil 104, this circuitry may be physically located in electronics housing 101. The electronics circuitry includes both control circuitry 400 and drive circuitry 410, which may be both fabricated on printed circuit board and encapsulated in housing 101.

The control circuitry 400 has a processor 401, with associated integrated circuit components: a program memory 402, a data memory 403, and clock circuit 404. Processor 401 is in data communication with these associated components by means of a bus 405. A PEMF program can be loaded into a microcontroller EPROM or other memory and installed as PEMF program memory 402. Alternatively, the PEMF program can be read into the PEMF program memory via an I/O port 406.

Data memory 403 may be used to store data about the patient's use of collar 100, based on an internally maintained clock and calendar provided by clock circuit 404. For example, PEMF program parameters—such as start time, stop time, duration, and daily average—may be stored in data memory 404. This data can be read out to a printer or to a communications link via the I/O port 406.

Processor 401 controls coil drive amplifier 407, which drives the energization and de-energization of coil 104. Coil break detection circuit 408 senses the electromagnetic fields output by coil 104 and provides a response signal to processor 401 for monitoring the operation of collar 100. Processor may store monitoring data in data memory 403, and will initiate an audible signal or other alarm in the case of malfunction.

Processor 401 receives power from a power source, such as a nine-volt lithium or alkaline battery, through a switching voltage regulator 409. Regulator 409 provides +5 volts power to processor 401 and its associated digital components.

Processor 401 and its associated components may be implemented with conventional integrated circuit devices. For example, processor 401 may be an Motorola 68HC11 processor. The data memory 403 and clock circuit 404 may be a Dallas Semiconductor Corporation device.

As explained further below in connection with FIGS. 7 and 8, the PEMF program outputs a pair of control signals, each comprising a series of pulse bursts. The two signals have their pulses offset, such that a pulse of one signal is high when a pulse of the other signal is low. These alternating control signals control the drive electronics so that it switches current on and off at the proper times to provide bi-phasic current for coil 104.

A feature of the control signals is that at the beginning of one of the pulse bursts, its first pulse is shorter than the other pulses in the same pulse train. Thus, for example, if the first pulse train has pulses with 65 microsecond on and 195 microsecond off times, then the first pulse of the first pulse train is 32.5 microseconds. This first short pulse sets up the magnetic field for the PEMF stimulation therapy signal in the single-winding coil. By turning on the drive circuitry for one-half pulse, energization of the magnetic field takes place to set the PEMF magnetic field away from zero. Then, the next pulse on the other pulse train turns on for 195 seconds. This sets the current so that the drive flyback energy goes in a negative direction. This causes current to flow from an initial negative direction. The current then ramps up through zero and increases from a negative number through zero to a positive number during the pulse.

Drive electronics 410 drives coil 104, so that coil 104 then generates the PEMF stimulation therapy signals. Drive electronics 410 has a first transistor switch 411 between break detection circuit 408 and coil 104, and a second transistor switch 412 between capacitance circuit 413 and coil 104. Switches 411 and 412 control the output signal from coil 104.

For initialization, switch 411 is turned on by coil drive amplifier 407 to present battery voltage across coil 104 for a period of one-half a normal pulse duration of typically 65 microseconds. Activation current flows through coil 104 to generate an output signal. When switch 411 switches off, switch 412 switches on to charge capacitance circuit 413 to a voltage equal to four times the battery voltage. This causes coil 104 to discharge in the opposite direction during the off period of switch 411 as compared to the direction during its on period. Thus, energy recovery occurs without a secondary coil. Drive circuit 410 permits sequencing of the current through coil 104 in both directions.

Therefore, for a given magnetic field strength, the peak current can be cut in half. This results in a factor of four reduction in $I^2R$ losses, where I is the instantaneous coil current and R is the resistance of the coil winding. These are the types of losses that would exist with the use of a secondary winding. The voltage $V_{X4}$ may be derived using the flyback pulse from coil 104, instead of requiring a separate voltage boost circuit. By balancing the capacity of capacitors 413a and 413b, it is possible to eliminate the need for a separate four-times voltage supply circuit.

In the example of FIG. 4, the capacitance circuit 413 is comprised of two series connected capacitors 413a and 413b. Their capacitance ratio is at least 1:3, and in the example of this description is 1:10 (in microfarads). Various other capacitor configurations could be used for capacitance circuit 413, with the common characteristic that it provide the desired energy restoring voltage, here $V_{X4}$. For example, capacitance circuit 413 could be comprised of a capacitor and voltage regulator circuitry.

Figure 5:
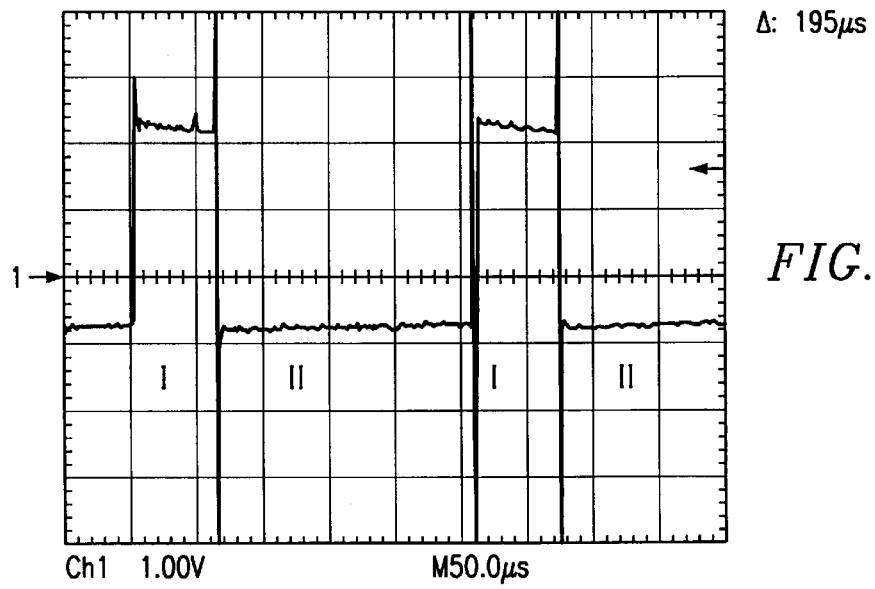
FIG. 5 shows an example of the waveform that the transducer coil generates.

FIG. 5 illustrates an example of an output waveform generated by coil 104. A pulse portion I is followed by pulse portion II. Pulse portion I has a duration of approximately 65 microseconds. Pulse portion II has a duration of approximately three times that of pulse portion I, or 195 microseconds. The voltage level for pulse portion I is approximately three times the voltage level for portion II. The areas of the portions I and II, therefore, are approximately equivalent. The output pulse periods (260 microseconds) and pulse frequency (3.84 kilohertz) of the output signal are in response to the pulsed drive signals.

Figure 6:
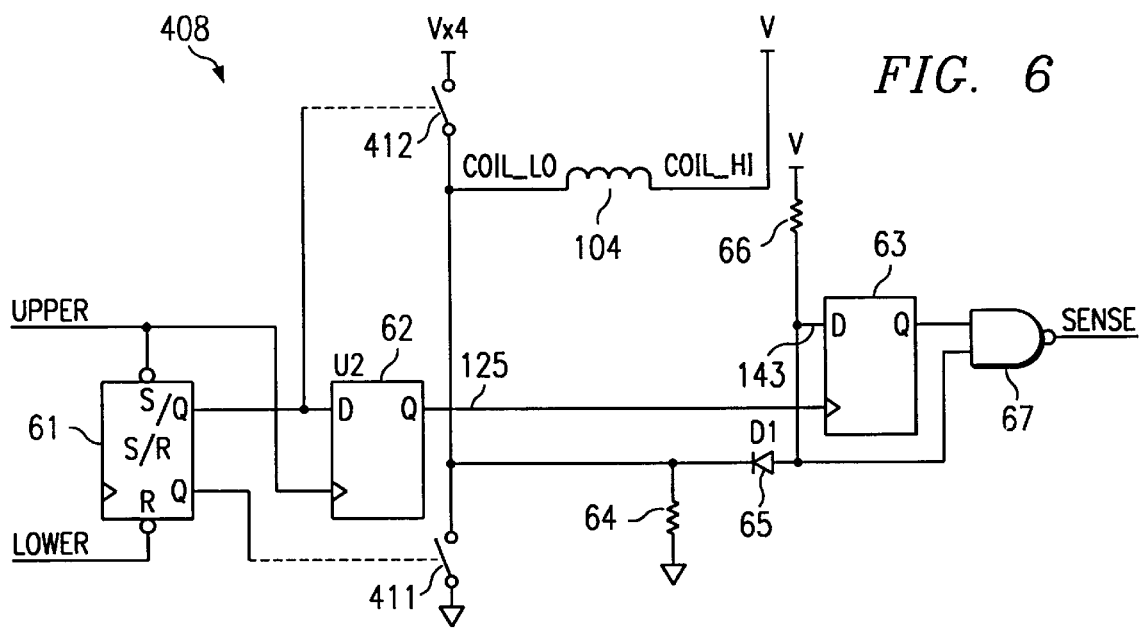
FIG. 6 is a schematic diagram of the coil break detection circuit of FIG. 4.

FIG. 6 illustrates one embodiment of coil break detection circuit 408. A set/reset flip-flop 61 receives an upper input signal and a lower input signal. One of its Q outputs goes to flip-flop 62 and controls the operation of switch 412. The other Q output controls the operation of switch 411. The Q output from flip-flop 62 goes to flip-flop 63 as a clock signal. Switch 412 controls whether the COIL_LO signal goes to $V_{X4}$, while switch 411 shunts COIL_LO to ground. The COIL_HI signal provides supply voltage V.

Resistor 64 and diode 65 receive supply voltage, V, from resistor 66. Flip-flop 63 receives as its D input the output from resister 66. The Q output from flip-flop 63 goes to NAND gate 67 to generate a sense output.

The voltage $V_{X4}$ is four times the voltage V, both being measured with respect to ground. The UPPER and LOWER signals consist of a burst of pulses, separated by an inter-burst period, as shown in FIG. 7. These two signals are essentially non-overlapping ensuring the stable operation of the S/R flip-flop 61. The Q outputs of S/R flip-flop 61 are of opposite state and are also essentially non-overlapping, ensuring that switches 411 and 412 are never simultaneously on.

During the inter-burst period, both switches 411 and 412 are open. Under normal operating conditions, the coil 104 will pull the COIL_LO signal level to the supply voltage V. If a break should occur in the coil, the COIL_LO signal will be pulled to ground by resistor 64.

Resistor 66, resistor 64, and diode 65 translate the COIL_LO signal to levels appropriate for the inputs of flip-flop 63 and NAND gate 67. The ratio of resistor 66 to resistor 64 is selected to provide a logic level "0" at the inputs of flip-flip 63 and NAND gate 67 should a break occur in coil 104.

The output of flip-flop 62 is a single pulse occurring at the beginning of a burst, beginning with the first pulse of UPPER and terminating on the second pulse of UPPER. The rising edge of the output of flip-flop 62 occurs prior to the first rising edge of COIL__LO due to the relatively short time delay associated with flip-flop 62 versus switch 412 and switch 411. The pulse output of flip-flop 62 goes to flip-flop 63, samples the inter-burst voltage. If the inter-burst voltage is equal to V, the Q output of flip-flop 63 is a logic level "1" until the next sampling pulse, thereby enabling output of the inverse of the COIL__LO signal to the processor 401 as the SENSE signal.

If the inter-burst voltage is at a ground level, due to a break in the coil 104, the output of flip-flop 63 is set to a logic level "0", disabling the output of the inverse of the COIL__LO signal to the processor.

A short across the coil terminals will cause the COIL__LO signal to be tied to V. The output of flip-flop 63 will be a logic level "1," therefore the output of NAND gate 67 will be a logical level "0" rather than the burst signal that processor 401 normally expects. This indicates the existence of a field fault condition. Connecting either the COIL__HI or COIL__LO terminal to ground, will essentially create a DC short.

Figures 7, 8:
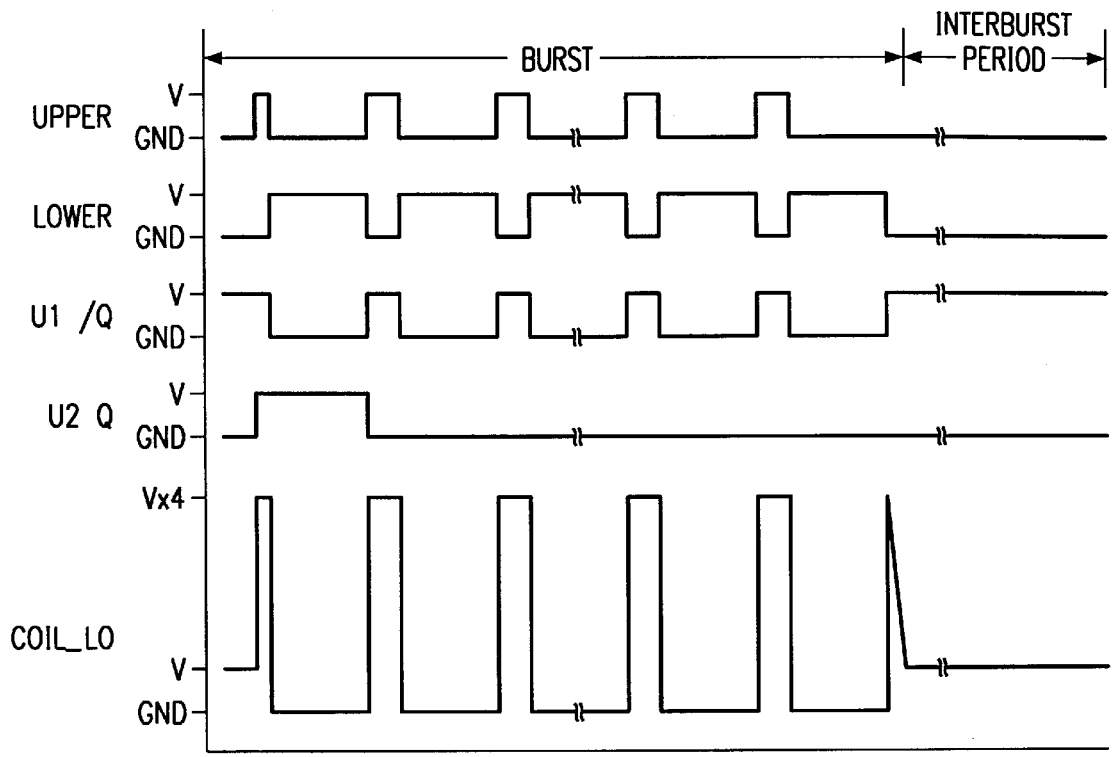
FIG. 7 illustrates the input logic burst signal provided to the transducer drive circuitry.
FIG. 8 is a table of drive signal parameters, which correspond to the diagrams of FIGS. 6 and 7.

FIG. 7 illustrates the timing relationship of the logic signals that drive switches 411 and 412, as well as signals internal to coil break detection circuit 408. In each logic burst signal, there are a number of pulses, the duration of each upper pulse being only one-third the duration of lower pulse. Other parameters may also be used.

FIG. 8 is a table of parameters, requirements, units, and symbols that correspond to the timing diagram of FIG. 7. In the table of FIG. 8, the burst period is 670 milliseconds, during which a first pulse width is 33 microseconds. Thereafter the upper pulse width is 65 microseconds. The lower pulse width is 195 microseconds. The pulse period is 260 microseconds for a pulse frequency of 3.84 kilohertz. For the example of FIG. 8, there are 99 pulses per burst. The invention may also use other timing parameters to achieve the desired PEMF signals and associated energy recovery operation.

As stated above, the use of only a single primary coil results in increased efficiency of transducer 20, as compared to designs using more than one coil. For the output PEMF signal described above, the energy recovery capacitance circuit 100 provides an energy recovery voltage of four times the source voltage provided by the battery. As explained above, both the source voltage (V) and the energy recovery voltage ($V_{4X}$) are lower than the voltages required for previous designs.

Other Embodiments

Although the invention has been described with respect to a specific, exemplary embodiment, various changes and modifications may be suggested to one skilled in the art. For example, the control and drive electronics may be different from those of the above-described embodiments. Therefore, it is intended that the invention encompass all changes and modifications that fall within the scope of the appended claims.

What is claimed is:

1. A collar for providing electromagnetic field therapy to a cervical region, comprising:
    a neck band having an approximately semicircular top profile with two ends, for placement around the back of a human neck;
    two chest straps, each strap attached at a first end to an end of the neck band;
    an electrical circuitry housing attached between the second ends of said chest straps, wherein the attachment of each chest strap is along a side of the housing, such that the housing is substantially fixed relative to the chest straps;
    electrical circuitry contained within said housing for generating an electrical drive signal; and
    at least one transducer coil attached to said neck band for generating an electromagnetic field in response to said drive signal.

2. The collar of claim 1, wherein said coil is shaped such that said coil curves around the sides of the neck.

3. The collar of claim 1, wherein said neck band and said coil are sufficiently flexible so as to permit said neck band and said collar to be adjusted to a given shape.

4. The collar of claim 1, further comprising a junction in at least one of said chest straps.

5. The collar of claim 4, wherein said junction is at an end of said chest strap, such that said chest strap is operable to disconnect from the housing.

6. The collar of claim 4, wherein said junction is at the ends of both said chest straps, such that said housing may be removed from said collar.

7. The collar of claim 1, wherein said electrical circuitry and said coil are battery powered.

8. The collar of claim 7, wherein said housing further comprises means for containing said battery.

9. The collar of claim 1 wherein said electrical circuitry comprises a circuit for recovering flyback energy from said coil and for sequencing current through said transducer coil in a positive direction and negative direction.

10. The collar of claim 1, wherein said chest straps are pivotally connected to said neck band.

11. The collar of claim 1, wherein said housing further has an on/off switch for said electrical circuitry.

12. The collar of claim 1, wherein said electrical circuitry comprises a processor for controlling said drive signal.

13. The collar of claim 1, wherein said neck band and said coil each have a flanged lower portion for extending down the neck of the patient.

14. The collar of claim 1, further comprising a control unit for controlling the on/off state of said electrical circuitry and for indicating said on/off state.

15. The collar of claim 14, wherein said control unit is attached to said housing.

16. The collar of claim 1, wherein said coil is embedded in said neck band.

17. The collar of claim 1, wherein said coil is made from a first material having a first flexible property and said neck band is made from a second material having a second flexible property.

18. The collar of claim 1, wherein said coil is deformable so as to take a desired shape in response to pressure and to hold said shape when said pressure is released and wherein said neck band is sufficiently flexible to permit said desired shape.

19. The collar of claim 1, wherein said neck band is deformable so as to take a desired shape in response to pressure and to hold said shape when said pressure is released and wherein said coil is sufficiently flexible to permit said desired shape.

20. The collar of claim 1, wherein the chest straps are generally flat in shape such that the flat side of the chest straps may rest against the chest of the wearer.

21. The collar of claim 1, further comprising one or more additional layers of material within the neckband.

* * * * *

UNITED STATES PATENT AND TRADEMARK OFFICE
CERTIFICATE OF CORRECTION

PATENT NO : 6,024,691
DATED : February 15, 2000
INVENTOR(S): John C. Tepper, Peter Kuo and Michael C. Dinsdale It is certified that error appears in the above-identified patent and that said Letters Patent are hereby corrected as shown below:

[73]    Assignee: AMEI Technologies Inc., Wilmington, Delaware

Signed and Sealed this

Seventeenth Day of April, 2001

Attest:

NICHOLAS P. GODICI

Attesting Officer        *Acting Director of the United States Patent and Trademark Office*